US00PP11131P

United States Patent [19]

Miyazaki

[11] Patent Number: Plant 11,131

[45] Date of Patent: Nov. 23, 1999

[54] TORENIA PLANT NAMED 'SUNRENIDIBU'

[75] Inventor: Kiyoshi Miyazaki, Kofu, Japan

[73] Assignee: Suntory Limited, Osaka, Japan

[21] Appl. No.: 08/927,081

[22] Filed: Sep. 10, 1997

[51] Int. Cl.[6] ..... A01H 5/00

[52] U.S. Cl. ..... Plt./263

[58] Field of Search ..... Plt./68.1, 263

[56] References Cited

PUBLICATIONS

Huxley et al. (Eds.) "Torenia", The New RHS Dictionary of Gardening, The Stockton Press New York. vol. 4 pp. 487, 1992.

UPOV CD–ROM Plant Breeder's Rights 9129, Japan, Torenia named Sanrenidhibu, 1996.

*Primary Examiner*—Howard J. Locker

*Assistant Examiner*—Melissa L. Kimball

*Attorney, Agent, or Firm*—Burns, Doane, Swecker & Mathis, L.L.P.

[57] ABSTRACT

Disclosed herein is a *Torenia hybrida* plant which has bi-colored brilliant purple and deep purple flower petals and a brilliant purple floral tube. The plant has semi-erect growth habit, medium branching and forms a great profusion blooms with the entire plant remaining in bloom for an extended period of time. The plant has a high resistance to heat, and moderate resistance to diseases and pests. The new variety has the ability to flower and to maintain its advantageous semi-erect growth habit even when grown in the shade.

2 Drawing Sheets

BACKGROUND OF THE VARIETY

The present invention relates to a new and distinct variety of *Torenia hybrida* plant obtained from crossing 'Crown Violet' (non-patented in the United States) (♀) and 'Con Color' (non-patented in the United States) (♂).

The Torenia (i.e., wishbone flower) is a very popular plant and is used for flower bedding and potting in the summer season. There are only a few varieties of the torenia plant which have a semi-erect growth habit, and a high resistance to heat and diseases. The typical Torenia plant needs full sunshine and hardly grows or flowers when grown in the shade. Accordingly, this invention was aimed at obtaining a new variety having a great profusion of flowers with brilliant purple and deep purple bi-colored flower petals and brilliant purple floral tube, a semi-erect growth habit, a high resistance to heat, a moderate resistance to diseases, and the ability to grow and flower in the shade while retaining a semi-erect growth habit. When typical torenia plants are grown in the shade, they commonly assume a spindly growth habit and no longer exhibit a semi-erect growth habit and tend not to flower.

The new variety of Torenia plant according to this invention is an interspecific hybrid originated from crossing the 'Con Color' variety of *Torenia* concolor as pollen parent and the 'Crown Violet' variety of *Torenia fournieri* having purplish-white flower petals as female parent.

Initially, 25 ovules were obtained from crossing the 'Con Color' variety and the 'Crown Violet' variety which has purplish-white flower petals in the spring of 1993 in the Hakushu Nursery Center of SUNTORY Ltd., 2913-1 Torihara, Hakushu-cho, Kitakoma-gun, Yamanashi-ken, Japan. More specifically, seven days after crossing the ovules were removed from ovaries and were cultured in vitro. These 25 ovules were sprouted, grown and plants were obtained. Subsequently they were grown in a bed and in pots as a trial beginning in the summer of 1993. The botanical characteristics of the plants were examined, using parent varieties 'Crown Violet' and 'Con Color', for comparison. As a result, only one plant was selected. It was concluded that this one torenia plant is distinguishable from any other variety, whose existence is known to us, and is uniform and stable in its characteristics following asexual reproduction by cuttings. This new variety of Torenia plant was named 'Sunrenidibu'.

In the following description, the color-coding is in accordance with The Horticultural Colour Chart of The Royal Horticultural Society, London, England (R.H.S. Color Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

*Torenia fournieri* 'Crown Violet' having violet petals was the female parent which was used in the formation of this new 'Sunrenidibu' variety, and was one of the Crown Series bred by the Sakata Seed Corp., Japan. The Crown Series includes plants having purplish blue flower petals, white flower petals, bi-colored of white and purplish blue and the like, and these plants are commonly characterized by a high resistance to heat and are commercially available in Japan. The main botanical characteristics of 'Crown Violet' are as follows.

Plant:
- *Growth habit*.—Erect.
- *Plant height*.—20–30 cm.
- *Plant width*.—30–50 cm.

Stem:
- *Diameter*.—3.0 mm.
- *Anthocyanin pigmentation*.—Present.
- *Branching*.—Slight.
- *Pubescence*.—Slight.
- *Length of internode*.—1–3 cm.

Leaf:
- *Phyllotaxis*.—Opposite.
- *Shape of blade*.—Ovate to ovate-lanceolate.
- *Apex*.—Acute.
- *Base*.—Cordate.
- *Length*.—2.0–4.0 cm.
- *Width*.—2.0–3.0 cm.

*Depth of incision.*—Deep.
*Color.*—Moderate olive green (R.H.S. 137A, JHS 3508).
*Pubescence.*—Slight.

Flower:
*Facing direction.*—Laterally.
*Diameter.*—2.0–3.0 cm.
*Height.*—20–30 mm.
*Color of floral tube.*—Soft violet (R.H.S. 92C, JHS 8008).
*Color of petal.*—Single color; purplish white (R.H.S. 62D, JHS 8001).
*Yellow eye color.*—Vivid yellow (R.H.S. 17C, JHS 2507).
*Calyx.*—1.5–2.0 cm in length.
*Anthrocyanin pigmentation of calyx limb.*—Present.
*Peduncle.*—1.5–2.0 mm in thickness; and 1.5–2.0 cm in length.
*Reproductive organs.*—1 pistil and 4 stamens.
*Anther color.*—White.
*Flowering duration.*—Medium.

Physiological and ecological characteristics: Low resistance to diseases and pests, high tolerances to heat, and low tolerance to cold. Typically this plant cannot maintain a semi-erect growth habit or flower well when grown in the shade.

*Torenia concolor* 'Con Color' which was used as the male parent in the crossing of this new 'Sunrenidibu' variety, is one of the Con Color Series bred by the Sakata Seed Corp., Japan. The Con Color Series includes plants having violet flower petal, bi-colored of strong purple and pale purple and the like, and these plants are commonly characterized by a high resistance to heat and are commercially available in Japan. The main botanical characteristics of 'Con Color' are as follows.

Plant:
*Growth habit.*—Decumbent.
*Plant height.*—10–15 cm.
*Plant width.*—50–70 cm.

Stem:
*Diameter.*—1.5 mm.
*Anthrocyanin pigmentation.*—Present.
*Branching.*—Profuse.
*Pubescence.*—Slight.
*Length of internode.*—4–6 cm.

Leaf:
*Phyllotaxis.*—Opposite.
*Shape of blade.*—Ovate to ovate-cordate.
*Length.*—1.0–2.0 cm.
*Width.*—1.0–2.0 cm.
*Depth of incision.*—Medium.
*Color.*—Moderate olive green (R.H.S. 137A, JHS 3508).
*Pubescence.*—Slight.

Flower:
*Facing direction.*—Laterally.
*Diameter.*—2.0–3.0 cm.
*Height.*—20–30 mm.
*Color of floral tube.*—Moderate Purple (R.H.S. 83B, JHS 8613).
*Color of petal.*—Single color, Deep purple (R.H.S. 89C, JHS 8311).
*Eye coloration.*—Lacking.
*Calyx.*—1.5–2.0 cm in length.
*Anthrocyanin pigmentation of calyx limb.*—Present.
*Peduncle.*—1.5–2.0 mm in thickness; and 3.0–5.0 cm in length.
*Reproductive organs.*—1 pistil and 4 stamens.
*Anther color.*—White.
*Flowering duration.*—Medium.

Physiological and ecological characteristics: High resistance to diseases and pests, high tolerances to heat, and low tolerance of cold.

SUMMARY OF THE VARIETY

The new variety of torenia plant has bi-colored flower petals with brilliant purple and deep purple and a brilliant purple floral tube. Accordingly, it is very different from the parent varieties 'Crown Violet' and 'Con Color'. The plant has semi-erect growth habit, medium branching and a great profusion blooms with the entire plant remaining in bloom for an extended period of time. The plant has a high resistance to heat, moderate resistance to diseases and pests, and forms flowers even when grown in the shade.

DESCRIPTION OF THE VARIETY

Figure 1:
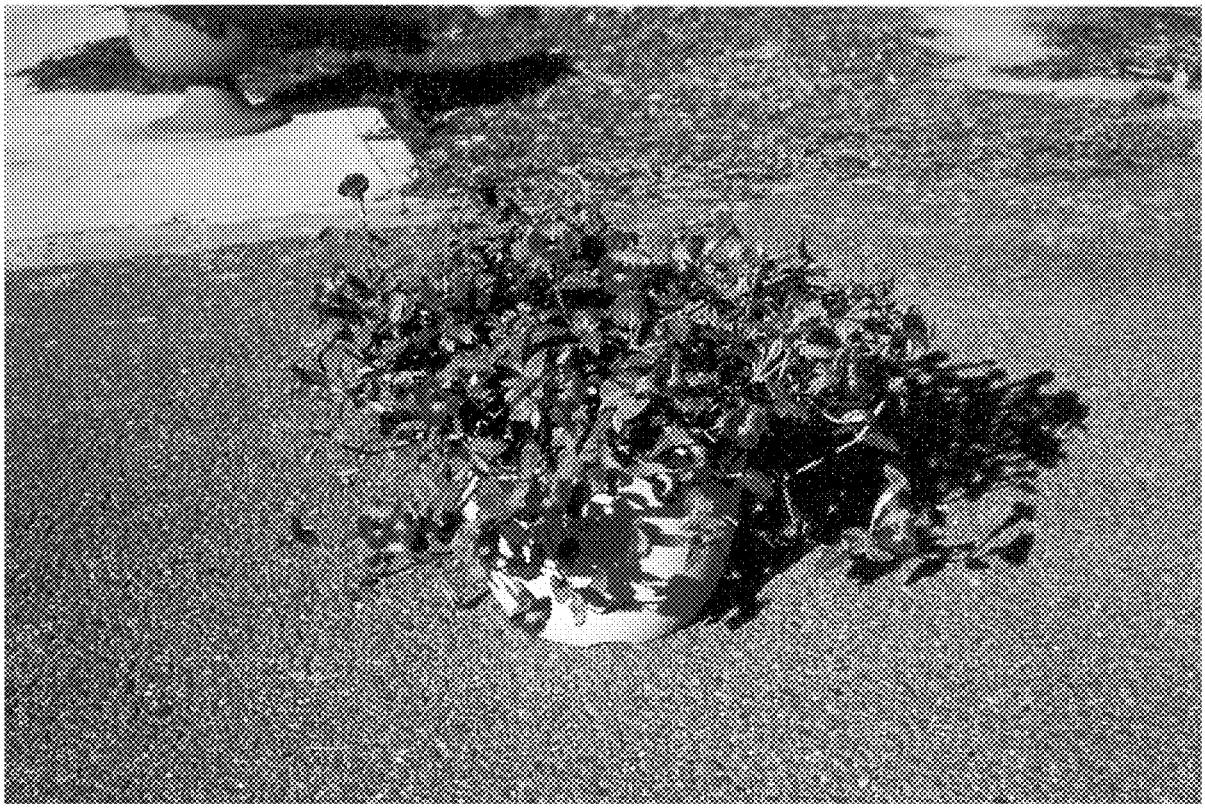
FIG. 1 is a photograph giving a partial view of the new variety of torenia plant when planted in a flower pot.
Figure 2:
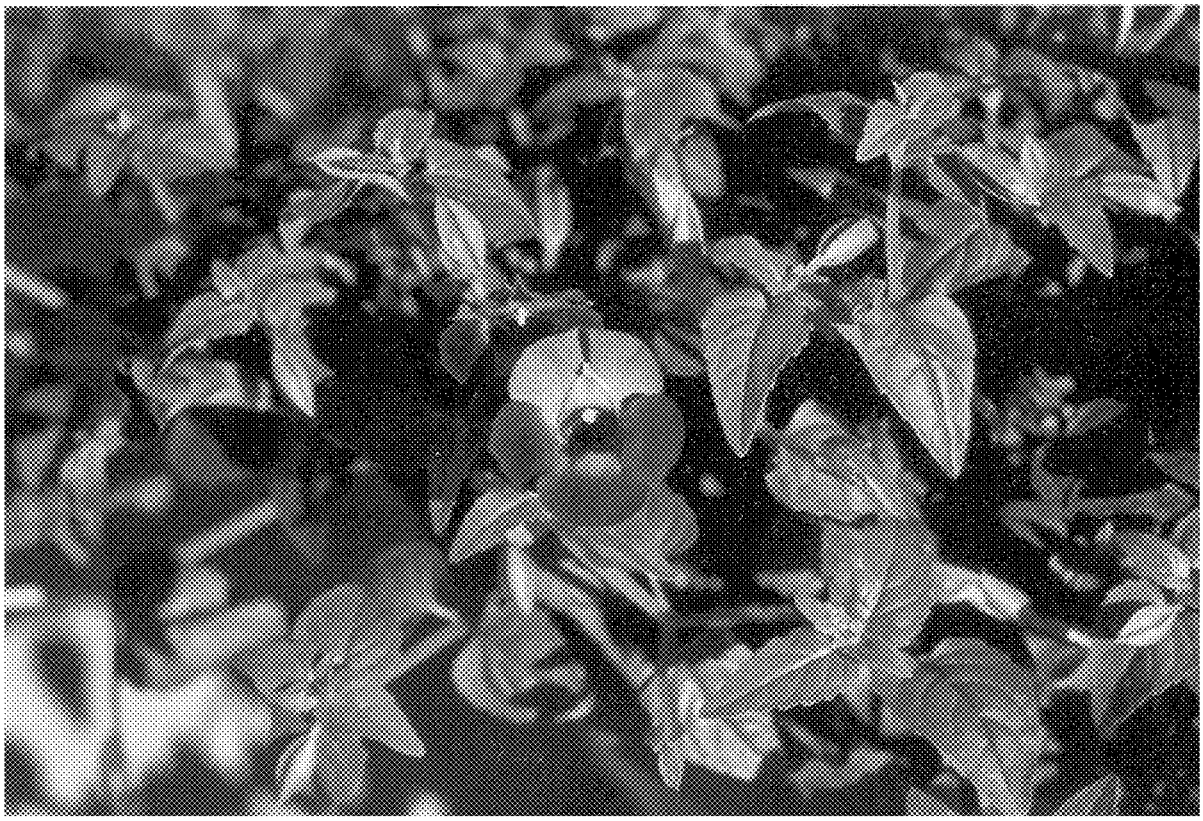
FIG. 2 is a close-up photograph of flowers of the new variety of torenia plant. The wishbone-shaped structure that is characteristic of the Torenia genus is visible. This is formed of two stamens that are fused at the anthers at the tip. One stamen pair is longer than the stigma and the other stamen pair is shorter than the stigma.

The botanical characteristics of the new and distinct 'Sunrendibu' variety of torenia plant are as follows.

Plant:
*Growth habit.*—Semi-erect. The stems hang down pliantly when potted in a hanging pot.
*Plant height.*—15–20 cm.
*Plant width.*—50–60 cm. The stem extends in a length of approximately 70 cm from the base.
*Growth.*—Medium branching, a great profusion of blooms with the entire plant remaining in bloom for an extended period of time.
*Blooming period.*—June to November in the southern Kanto area, Japan and June to October in the Tokyo area, Japan. The plant shape does not change throughout this period.

Stem:
*Diameter.*—2.0–3.0 mm.
*Anthocyanin pigmentation.*—Present.
*Branching.*—Medium. Similar to *Torenia fournieri.*
*Pubescence.*—Slight.
*Color.*—Yellow-Green (R.H.S. 144A, JHS 3507).
*Length of internode.*—4–6 cm.

Leaf:
*Phyllotaxis.*—Opposite.
*Shape of blade.*—Ovate to ovate-cordate.
*Apex.*—Obtuse.
*Base.*—Cordate.
*Length.*—2.0–3.0 cm.
*Width.*—1.5–2.5 cm.
*Depth of incision.*—Medium.

*Color*.—Moderate olive green (R.H.S. 146A, JHS 3508) on the upperside and yellow-green (R.H.S. 144A, JHS 3507) on the underside.

*Pubescence*.—Slight.

Flower:

*Facing direction*.—Laterally. One or two flowers commonly appear axillarily from a node of the stem.

*Diameter*.—Approximately 2.0–3.0 cm.

*Height*.—Approximately 30–40 mm.

*Color of floral tube*.—Brilliant purple (R.H.S. 84A, JHS 8305).

*Color of petal*.—Bi-colored, upper petal: brilliant purple (R.H.S. 84A, JHS 8305), lower petal: deep purple (R.H.S. 86A, JHS 8307). The upper petal and the lower petal commonly tend to be lighter towards the base.

*Calyx*.—1.0–2.0 cm in length.

*Anthocyanin pigmentation of calyx limb*.—Present.

*Peduncle*.—1.5–2.0 mm in thickness; and 2.0–3.0 cm in length.

*Fragrance*.—None.

*Reproductive organs*.—1 pistil and 4 stamens.

*Anther color*.—White.

*Flowering duration*.—Individual blooms commonly last approximately three to four days. Pinching typically is not necessary to ensure continued blooming. However, pinching often will lead to the formation of more branches and will thereby further enhance the form of the plant.

*Fertility*.—Male and female sterile. No seeds have been observed to date.

Physiological and ecological characteristics: Medium resistance to diseases and pests, high tolerance to heat, and low tolerance to cold. The plant has the ability to flower and maintain its desired semi-erect growth habit even when grown in the shade.

This new 'Sunrendibu' variety of Torenia plant is particularly suited for use as attractive ornamentation when grown in hanging flower baskets and in planters.

I claim:

1. A new and distinct variety of *Torenia hybrida* plant having the following combination of characteristics:

(a) exhibits a semi-erect growth habit,
(b) forms in abundance attractive bi-colored brilliant purple and deep purple blossoms over an extended period of time,
(c) well tolerates growing in the shade, and
(d) exhibits good resistance to heat;

substantially as illustrated and described.

* * * * *